(12) United States Patent
Levy

(10) Patent No.: US 9,107,797 B2
(45) Date of Patent: Aug. 18, 2015

(54) SEXUAL STIMULATION DEVICES AND METHODS

(71) Applicant: Tricatalyst, LLC, Berkeley, CA (US)

(72) Inventor: David H. Levy, Berkeley, CA (US)

(73) Assignee: Tricatalyst, LLC, Berkeley, CA (US)

( * ) Notice: Subject to any disclaimer, the term of this patent is extended or adjusted under 35 U.S.C. 154(b) by 217 days.

(21) Appl. No.: 13/826,788

(22) Filed: Mar. 14, 2013

(65) Prior Publication Data

US 2013/0197302 A1  Aug. 1, 2013

Related U.S. Application Data

(63) Continuation-in-part of application No. 12/539,529, filed on Aug. 11, 2009, now Pat. No. 8,647,255.

(60) Provisional application No. 61/087,821, filed on Aug. 11, 2008.

(51) Int. Cl.
*A61H 21/00* (2006.01)
*A61H 23/02* (2006.01)
*A61H 19/00* (2006.01)
*A61F 5/41* (2006.01)

(52) U.S. Cl.
CPC .............. *A61H 23/02* (2013.01); *A61H 19/44* (2013.01); *A61F 2005/412* (2013.01); *A61H 23/0218* (2013.01); *A61H 23/0263* (2013.01); *A61H 2201/0153* (2013.01); *A61H 2201/123* (2013.01); *A61H 2201/149* (2013.01); *A61H 2201/1418* (2013.01); *A61H 2201/1666* (2013.01); *A61H 2201/1669* (2013.01); *A61H 2201/501* (2013.01); *A61H 2201/5064* (2013.01)

(58) Field of Classification Search
CPC ... A61H 23/02; A61H 19/44; A61H 23/0218; A61H 23/0263; A61H 2201/501; A61H 2201/149; A61H 2201/1666; A61H 2201/123; A61H 2201/0153; A61H 2205/412
USPC .......... 600/38–41; 601/78, 80, 81, 82, 83, 84, 601/97, 101
See application file for complete search history.

(56) References Cited

U.S. PATENT DOCUMENTS

| | | | |
|---|---|---|---|
| 494,410 | A | 3/1893 | Carpenter |
| 734,498 | A | 7/1903 | Bachler |
| 1,413,789 | A | 4/1922 | Douglas |
| 1,729,296 | A | 9/1929 | David |
| 3,259,132 | A | 7/1966 | Katter |
| 3,495,589 | A | 2/1970 | Clement |
| 3,598,106 | A | 8/1971 | Buning |
| 3,752,150 | A | 8/1973 | Harris |

(Continued)

FOREIGN PATENT DOCUMENTS

| | | |
|---|---|---|
| WO | WO8806077 A2 | 8/1988 |
| WO | WO2009152813 A1 | 12/2009 |

*Primary Examiner* — Samuel Gilbert
(74) *Attorney, Agent, or Firm* — Fish & Richardson P.C.

(57) ABSTRACT

A sexual stimulation device includes an elongated dildo housing sized to be received within an orifice of a human body, the housing defining an internal cavity extending along a longitudinal axis of the housing, a mass laterally constrained within the cavity and movable linearly along the cavity, and an electrically driven actuator disposed within the housing and operably coupled to the mass. The actuator is operable to accelerate the mass along the cavity and to thereby induce a longitudinal reactive acceleration of the housing.

25 Claims, 2 Drawing Sheets

(56) References Cited

U.S. PATENT DOCUMENTS

| | | |
|---|---|---|
| 3,991,751 A | 11/1976 | O Rourke |
| 3,996,930 A | 12/1976 | Sekulich |
| 4,050,449 A | 9/1977 | Castellana et al. |
| 4,167,938 A | 9/1979 | Remih |
| 4,776,347 A | 10/1988 | Matthews |
| 5,072,720 A | 12/1991 | Francis et al. |
| 5,131,906 A | 7/1992 | Chen |
| 5,231,336 A | 7/1993 | van Naman |
| 5,256,123 A | 10/1993 | Reinbolt |
| 5,573,499 A | 11/1996 | McAllister |
| 5,593,381 A * | 1/1997 | Tannenbaum et al. ......... 601/93 |
| 5,674,238 A | 10/1997 | Sample et al. |
| 5,690,603 A | 11/1997 | Kain |
| 5,690,605 A | 11/1997 | Hamlin et al. |
| 5,704,894 A | 1/1998 | Boutos |
| 5,724,994 A | 3/1998 | Simon et al. |
| 5,782,818 A | 7/1998 | Shubin |
| 5,806,523 A | 9/1998 | Shubin |
| 5,807,360 A | 9/1998 | Shubin |
| 5,885,205 A | 3/1999 | Kassman |
| 6,039,703 A | 3/2000 | Badilla |
| 6,165,108 A | 12/2000 | Ralston |
| 6,179,795 B1 | 1/2001 | Garza |
| 6,251,066 B1 * | 6/2001 | Pack ............... 600/38 |
| 6,368,268 B1 | 4/2002 | Sandvick et al. |
| 6,423,017 B2 | 7/2002 | Brotz |
| 6,632,185 B2 * | 10/2003 | Chen ............... 601/101 |
| 7,079,898 B2 * | 7/2006 | Cohn ............... 607/45 |
| 7,104,950 B2 | 9/2006 | Levy |
| 7,238,163 B1 | 7/2007 | Fried et al. |
| 7,608,037 B2 | 10/2009 | Levy |
| 2003/0069470 A1 * | 4/2003 | Lee ............... 600/38 |
| 2003/0073881 A1 | 4/2003 | Levy |
| 2004/0082831 A1 * | 4/2004 | Kobashikawa et al. ......... 600/38 |
| 2010/0041944 A1 | 2/2010 | Levy |
| 2010/0222723 A1 * | 9/2010 | Hoffmann ............... 601/107 |
| 2011/0144426 A1 | 6/2011 | Blenk et al. |
| 2013/0281776 A1 | 10/2013 | Levy |

\* cited by examiner

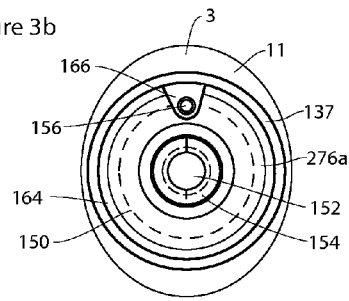
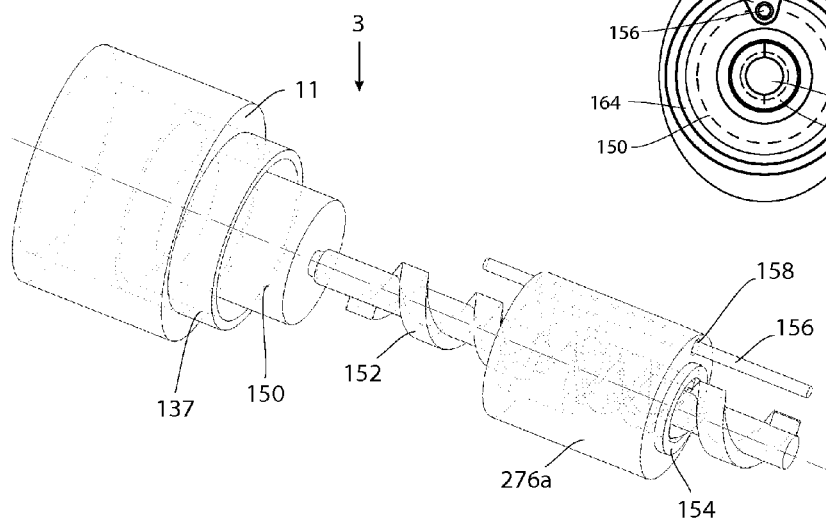
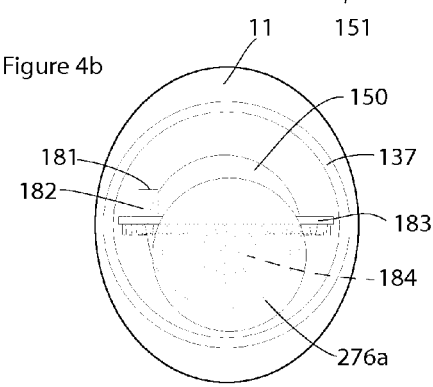
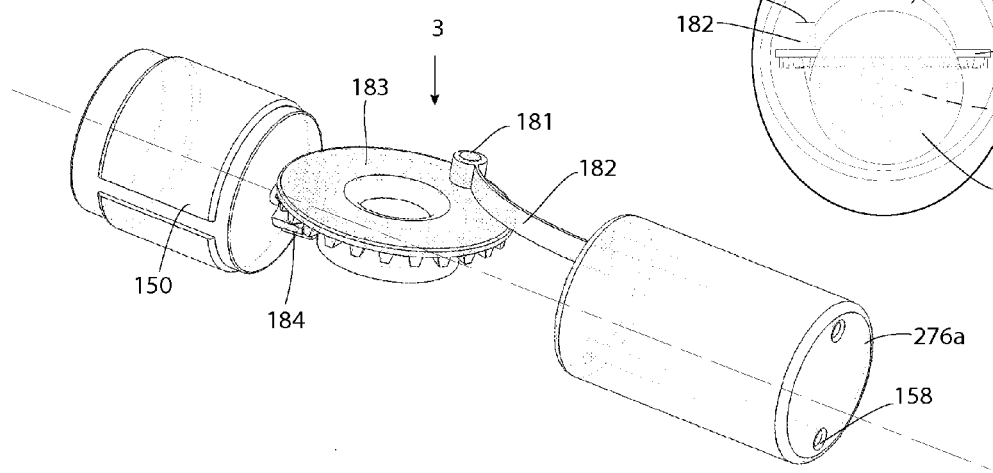

SEXUAL STIMULATION DEVICES AND METHODS

CROSS-REFERENCE TO RELATED APPLICATIONS

This application is a continuation-in-part of co-pending U.S. application Ser. No. 12/539,529 (Sexual Stimulation Devices and Methods) filed Aug. 11, 2009, which claims the benefit of U.S. provisional application Ser. No. 61/087,821 (Sexual Stimulation Devices and Methods) filed Aug. 11, 2008, the entire disclosures of both of which are incorporated herein by reference.

TECHNICAL FIELD

This invention relates to devices and methods to sexually stimulate the human body.

BACKGROUND

Vendors today manufacture vibrators with a small mass (typically under 5 grams), with high frequency (typically 200 to 1000 RPM) and with the mass located off-center on a rotary motor. These devices are characterized by providing non-motile vibration. While popular, one of the known limitations of these products is that high frequency vibration can desensitize the sexual response, thereby making non-vibratory sexual relations more difficult. There are also phallus-shaped devices that provide very low frequency, high amplitude thrusting motions designed to mimic the sexual act without necessitating motion of the base. Such devices can be "stand-alone" (i.e., with one end immovably constrained) or hand held. Both seek to mimic the thrusting motions of intercourse.

SUMMARY

According to one aspect of the invention, a sexual stimulation device includes an elongated dildo housing sized to be received within an orifice of a human body, the housing defining an internal cavity extending along a longitudinal axis of the housing, a mass laterally constrained within the cavity and movable linearly along the cavity, and an electrically driven actuator disposed within the housing and operably coupled to the mass. The actuator is operable to accelerate the mass along the cavity and to thereby induce a longitudinal reactive acceleration of the housing.

In some examples, wherein the housing comprises a flexible sheath overlaying a structural member.

In some embodiments, the actuator comprises a linear motor or an electromechanical solenoid. The mass may include an armature of the solenoid. In some cases, a majority of the mass is disposed outside of a coil of the solenoid. In some cases, the mass includes a weight removably attached to the solenoid armature. For many applications, the solenoid has an armature slidably disposed within a solenoid bore having a diameter of between about 1.5 and 10 mm.

Some embodiments also include a lateral mass displaceable with respect to the housing only in a direction substantially perpendicular to the longitudinal axis.

In some configurations the actuator includes a rotary motor coupled to a transmission that converts rotary motor armature motion to linear mass motion. For example, the transmission may include a screw shaft disposed within a nut element constrained against rotation with respect to the housing. In another example, the transmission includes a first gear secured to an armature of the motor, and a second gear operably coupled to the first gear and mounted to rotate about an axis perpendicular to the motor armature. A connecting link, such as a flex spring or a rigid connecting rod, may rotatably connected to an offset pivot point of the second gear and attaching the second gear to the mass.

Preferably, the actuator is operable to move the mass a longitudinal distance of at least 10 mm, in some cases at least 20 mm, with respect to the housing.

Some examples include a signal receiver connected to the actuator and responsive to a control signal from a remote operator.

Some examples include a controller configured to control motion of the mass according to a preset motion profile. In some cases, the motion profile includes a first acceleration rate in a first direction along the longitudinal axis, and a second acceleration rate in a second direction along the longitudinal axis, the second acceleration rate differing from the first acceleration rate.

Some embodiments also include an internal power source, such as one or more batteries, disposed within the housing and connected to the actuator through a switch and/or a controller.

Some embodiments also include a handle disposed at one end of the dildo housing, with an isolator connecting the dildo housing and handle. The dildo housing may be slidably coupled to the handle, for example.

Preferably, the actuator is operable to induce an overall longitudinal motion of the device, the induced overall motion having an amplitude of at least 4 mm.

The actuator is preferably operable to induce an overall longitudinal motion of the device with an amplitude at least 10 times greater than an amplitude of any lateral motion of the device induced by actuator operation.

In some examples the mass is of a non-ferromagnetic material, such as lead or tungsten.

Another aspect of the invention features a method of creating sexual stimulation. The method includes bringing the above-described device into contact with a sexual organ, and holding the device in contact with the sexual organ while the actuator is operated to move the mass along the cavity.

Another aspect of the invention features a massage device with a cylindrical housing, an electromechanical arrangement disposed in the housing for generating mechanical vibrations, an electronic controller for controlling the electromechanical arrangement, and a power source electrically coupled to the electromechanical arrangement and the electronic controller. The electromechanical arrangement includes at least one coil element and at least one ferromagnetic core arranged parallel or coaxial with the coil element and movably guidable parallel to a cylinder axis of the housing.

Embodiments of this invention may be advantageously configured to provide a stimulation that may be different from the thrusting motion of intercourse and yet not as desensitizing to the sexual organs as some known devices and methods. This different stimulation may be oscillatory, but with a frequency lower than provided by typical rotary vibrators with an off-center mass. Some examples may be capable of providing stimuli that are varied, controllable, and subtle. The variable sensation may be independent of any thrusting motion imposed on the device by the hand of the user, and the variable sensation may be dependent on the thrusting motion in a variety of predictable and semi-predictable and non-predictable ways. The sensation may be dynamically variable, or under dynamic control, whether the user is co-located, or distant.

DESCRIPTION OF DRAWINGS

FIG. 3a shows an exposed isometric view of the mechanics of a dildo with linear vibration, large mass, and a screw actuator.

FIG. 3b shows an exposed end view of the dildo of FIG. 3a

FIG. 4a shows an exposed isometric view of the mechanics a dildo with motile vibration, large mass, and a rotary actuator.

FIG. 4b shows an exposed end view of the dildo of FIG. 4a.

Like reference symbols in the various drawings indicate like elements.

DETAILED DESCRIPTION

Figure 1:
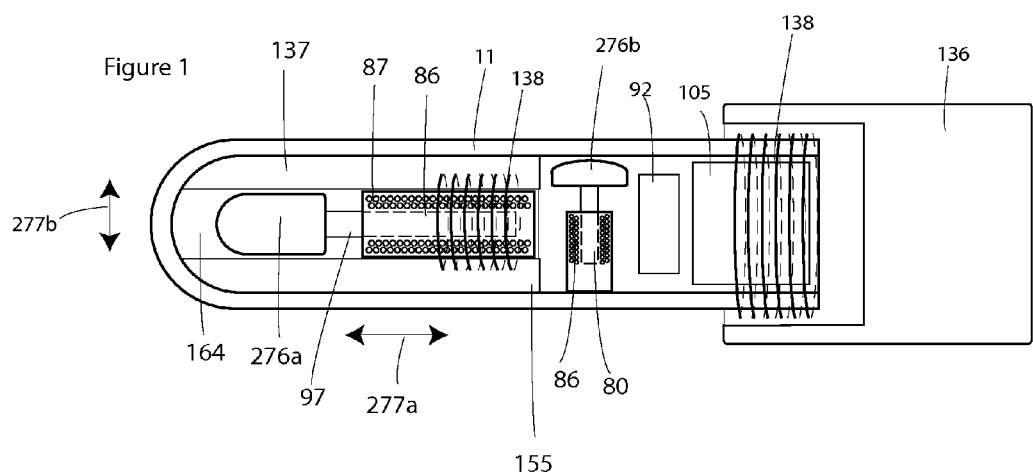
FIG. 1 is a sectional view of a dildo with a linear vibration, large masses and linear actuators.

FIG. 1 shows a sexual pleasure device 3 with a linear displacement actuator 80 oriented radially, and accelerating a mass 276b and a second linear displacement actuator 80 oriented axially, and accelerating a mass 276a within the device. The weight of each of the accelerated masses 276a and 276b (calculated separately along each axis) is selected according the desired performance dictated by MV=mv where:

m—mass of the accelerated mass (276a or 276b)

v=the velocity imposed upon the accelerated mass by its displacement actuator

M=the mass of the device, less the accelerated mass

V=the velocity of the device as it physically displaces along the axis of motion.

Compared to some known sexual stimulation products containing accelerated masses, in this device the accelerated mass is substantially increased, the frequency is substantially decreased, the motion of the mass is linear, and the mass drive mechanism is internal to the device. The objective is to provide a sensation that is not vibratory, but rather a physical displacement of the device that is superimposed on the self-directed hand motion. Unlike the prior art, this embodiment is capable of a single oscillation cycle providing a significant sensation to a user, because a measurable degree of motion and hence friction is felt, as opposed to merely non-motile vibration. This additional motion may be along the major axis, as provided by mass 276a and its associated linear displacement actuator 80 (providing a displacement force along axis 277a), or may be along the a radial axis, as provided by mass 276b and its associated linear displacement actuator 80, providing a displacement force along axis 277b. Linear displacement actuators 80 include two types: the first is electromechanical solenoid 86, typically a metal rod or metal core 97 within a coil of wire (often with a return spring) typically used for transient force application with a low degree of control. In one example, the diameter of the metal core 97 is in the range from 1.5 mm to 10 mm. Field strength in a solenoid is independent of diameter. Therefore, a benefit of small diameter metal cores 97 is to reduce the amount of conductor (typically copper) needed to manufacture the associated solenoid. The second type of linear actuator 80 is a linear motor 87, typically a magnet (or magnets) placed within a magnetic field and typically used for higher degrees of control. Creating motion of a magnet by flowing electrical current through a wire and using induction to move a rod within a solenoid is disclosed in high school physics texts. Masses 276a and 276b may be made from any dense material such as steel, lead or tungsten. In one embodiment, each mass 276a (or 276b) and its associated linear displacement actuator 80 are separate elements. In the preferred embodiment the cross section of mass 276a and 276b is round, but other cross-sections are envisioned.

The housing of the device may include an elastomeric sheath over an internal housing 137. The user's hand may be shielded from the motions of the device through an isolation mechanism 44 located between handle 136 and internal housing 137 or shaft 155. Isolation mechanism 44 may include a spring element 138 or a sliding mechanism, (such as a protruding wall in a groove or a flexure) that allows low friction linear motion between the shaft 155 and the handle 136.

In one embodiment the displacement of mass 276a or mass 276b is at least 10 mm. In another embodiment, displacement of mass 276a or 276b is at least 20 mm. The amplitude and acceleration curves may be varied, as well as the frequency, thereby enabling a wide range of sensations to the user. For example, one embodiment provides multiple sequential stimuli in a single direction. A specific example of this embodiment is overall travel distance (X) of a linear displacement actuator 80 of 27 mm in which the device provides three sequential and discrete movements (i.e. "thumps") of approximately 9 mm each, all in a first direction without recoiling. In one embodiment the controller 92 initiates a plurality of such sequential unidirectional discrete motions in a relatively short time, thereby providing a distinctly different sensation than simple oscillation. In one embodiment the device traverses the two longitudinal directions (i.e., in and out or plus and minus) at distinctly different rates, moving in a first direction at a high rate of speed/acceleration, thereby noticeably displacing the device (and providing the associated sensation of displacement) and subsequently returning in the opposite direction at a significantly slower rate such that the recoil and the associated motion of the device 3 is substantially smaller, if detected at all. This pattern may be repeated, thereby providing the sensation that the device is only thrusting in a single direction. By modifying the acceleration curves, displacements and sequences in this manner, a wide range of novel sensations may be provided. In one example controller 92 includes input from a wireless transceiver such as Bluetooth or Wi-Fi disposed within dildo 3, thereby enabling communication to the Internet and cellular communications.

Displacement of the device in an operational mode may be measured in the following manner: The device is first fixed, in a horizontal position, to a support with a smooth bottom surface. The support, including any material used to fix the device to the support, must weigh less than 1/100 of the weight of the device. The supported device is then placed on an air table, such that a flow of air from the table maintains the support slightly elevated and free of lateral motion constraint. The device is then turned on and the external motion measured optically with respect to the air table. If lateral (non-longitudinal) motion is to be measured, the device should be mounted such that the direction of motion of the internal lateral mass is parallel to the table surface.

Preferably, the motion of the longitudinally accelerated internal mass will induce an overall motion of the device with an amplitude of at least 4 mm. It is also preferred, for many applications, that the longitudinal motion be at least 10 times greater in amplitude than any lateral (non-longitudinal) motion of the device.

Figure 2:
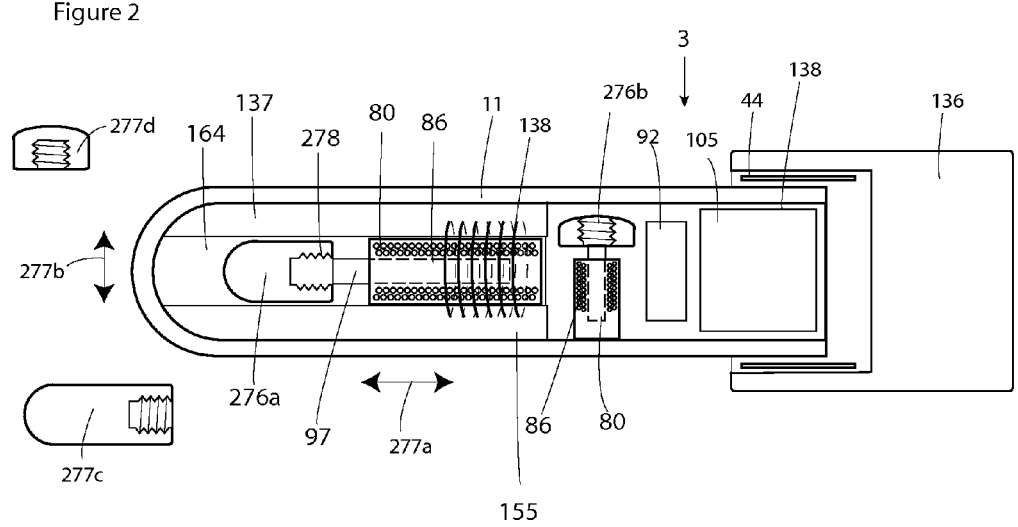
FIG. 2 is a sectional view of a dildo with linear vibration, interchangeable masses, and linear actuators.

FIG. 2 shows an embodiment in which masses 276a and 276b are interchangeable with masses 276c and 276d, respectively. Interchangeable masses allow the physics of the device to be altered without needing to redesign other features of the product. Interchangeability is provided by locking mechanism 278, shown here as a tapped hole in masses 276a and 276b and a threading on the end of metal rod 97. Locking mechanism 278 may also be provided by a press fit between the two components. FIG. 2 also shows isolation mechanism 44 embodied with a low friction bearing surface 139 such as Teflon allowing internal housing 137 (or shaft 155) to slidingly engage with handle 136.

FIG. 3a shows a dildo 3 with linear vibration in which linear actuator 80 includes a high-helix screw 152 rotated by rotary electric motor 150. Mass 276a is coupled to screw 152 through a low friction nut 154 which is itself permanently affixed to mass 276. Mass 276 is restrained from rotation with respect to the body of motor 150. In this embodiment, mass 276 is constrained from rotation about screw 152 by alignment rod 156, which extends through hole 158, itself disposed as far as possible from major axis 151. Alignment rod 156 is rigidly secured to internal housing 137. Internal housing 137 extends to cover and protect screw 152 and the motion of mass 276a, but has been cut back in this figure to expose the inner structures. Likewise, the controller and battery have been omitted for clarity.

In an alternate example, mass 276a is constrained from rotation by a channel or ridge slidingly engaged with a corresponding ridge or channel in internal housing 137. Any structure that prevents mass 276 from rotating while permitting displacement along major axis 151 without imposing high friction will suffice. Because the motion is oscillatory, it is important for nut 154 to closely engage with the threads of screw 152. Techniques (such as opposed bearing surfaces including a spring force) or simply manufacturing with a high tolerance and low-wear/low-friction materials such as Teflon are known in the art. Similar connections are used in many consumer products to provide high accuracy, such as in printers and copiers. In this product the accuracy required is far lower, and the accelerated mass 276a is in the place of a print head or scanner element. The lower accuracy allows tolerances and related cost to be lower.

FIG. 3b illustrates how alignment rod 156 is connected to internal housing 137 by flange 166, and that the external contour of sheath 11 may be related to the shape of the internal housing 137. The preferred shape of the cavity 164 that contains mass 276a or 276b is round, but other shapes are within the scope of the invention. Likewise, mass 276a may be constrained to travel in a slight arc (i.e., similar to a real phallus) and still be considered to be "linear" as that term is used here.

FIG. 4a shows an example of dildo 3 with linear vibration in which a drive point 181 translates in a circle disposed in a plane proximate to the major diameter of the housing. In this example drive point 181 is disposed near the edge and on the back of large diameter gear 183 which is mounted for rotation with respect to the housing and driven by a small gear 184 fixed to the output shaft of rotary electric motor 150. A variety of means can be used to oscillate mass 276a or 276b through drive point 181. In this figure, a pin is co-molded with large diameter gear 183 at drive point 181 and a flex spring 182 is rigidly attached to mass 276a (or a molded carrier housing containing mass 276a) at one end and the other end of flex spring 182 is molded with a hole to accommodate the offset pin on gear 183. The details of the bearings and assembly features such as screws and washers are well-known in the art and not shown. Other variations are possible. For example, flex spring 182 may be replaced with a rigid linkage that allows rotation at both ends, or with a tension member such as a string and to attach a spring to mass 276a or 276b in opposition to the tension member. Other mechanisms may use cams, barrel cams, eccentric wheels, and other linkages to couple the rotary output from electric motor 150 to mass 276a or 276b to translate rotary motion in a first plane to oscillatory motion in a perpendicular plane. Common to all previous examples, mass 276a or 276b oscillates as described in FIG. 1.

FIG. 4b illustrates how drive point 181 and large diameter gear 183 are disposed proximate to the middle of housing. In most cross-sections, the middle will also correspond with the point that is largest and most suitable for large diameter gear 183.

While a number of examples have been described for illustration purposes, the foregoing description is not intended to limit the scope of the invention, which is defined by the scope of the appended claims. There are and will be other examples and modifications within the scope of the following claims.

What is claimed is:

1. A sexual stimulation device, comprising:
   an elongated dildo housing sized to be received within an orifice of a human body, the housing defining an internal cavity extending along a longitudinal axis of the housing;
   a mass laterally constrained within the cavity and movable linearly along the cavity; and
   an electrically driven actuator disposed within the housing and operably coupled to the mass, the actuator operable to accelerate the mass with a non-rotational, linear reciprocal motion along the cavity and to thereby induce a longitudinal reactive acceleration of the housing.

2. The device of claim 1, wherein the housing comprises a flexible sheath overlaying a rigid shell extending about the internal cavity.

3. The device of claim 1, wherein the actuator comprises a linear motor.

4. The device of claim 1, wherein the actuator comprises an electromechanical solenoid.

5. The device of claim 4, wherein the mass includes an armature of the solenoid.

6. The device of claim 4, wherein a majority of the mass is disposed outside of a coil of the solenoid.

7. The device of claim 4, wherein the mass includes a weight removably attached to the solenoid armature.

8. The device of claim 4, wherein the solenoid comprises an armature slidably disposed within a solenoid bore having a diameter of between about 1.5 and 10 mm.

9. The device of claim 1, further including a lateral mass displaceable with respect to the housing only in a direction substantially perpendicular to the longitudinal axis.

10. The device of claim 1, wherein the actuator comprises a rotary motor coupled to a transmission that converts rotary motor armature motion to linear mass motion.

11. The device of claim 10, wherein the transmission comprises a screw shaft disposed within a nut element constrained against rotation with respect to the housing.

12. The device of claim 10, wherein the transmission comprises a first gear secured to an armature of the motor, and a second gear operably coupled to the first gear and mounted to rotate about an axis perpendicular to the motor armature.

13. The device of claim 1, wherein the actuator is operable to induce an overall longitudinal motion of the device with an amplitude at least 10 times greater than an amplitude of any lateral motion of the device induced by actuator operation.

14. The device of claim 1, wherein the mass is of a non-ferromagnetic material.

15. The device of claim 1, wherein the actuator is operable to move the mass a longitudinal distance of at least 10 mm with respect to the housing.

16. The device of claim 15, wherein actuator is operable to move the mass a longitudinal distance of at least 20 mm with respect to the housing.

17. The device of claim 1, further comprising a signal receiver connected to the actuator and responsive to a control signal from a remote operator.

18. The device of claim 1, further comprising a controller configured to control motion of the mass according to a preset motion profile.

19. The device of claim 18, wherein the motion profile includes a first acceleration rate in a first direction along the longitudinal axis, and a second acceleration rate in a second directions along the longitudinal axis, the second acceleration rate differing from the first acceleration rate.

20. The device of claim 1, further comprising a handle disposed at one end of said dildo housing, and an isolator connecting the dildo housing and handle.

21. The device of claim 20, wherein the dildo housing is slidably coupled to the handle.

22. The device of claim 1, wherein the actuator is operable to induce an overall longitudinal motion of the device of at least 4 mm.

23. A method of creating sexual stimulation, the method comprising
bringing the device of claim 1 into contact with a sexual organ; and
holding the device in contact with the sexual organ while the actuator is operated to move the mass along the cavity.

24. A sexual stimulation device, comprising:
an elongated dildo housing sized to be received within an orifice of a human body, the housing defining an internal cavity extending along a longitudinal axis of the housing;
a mass laterally constrained within the cavity and movable linearly along the cavity; and
an electrically driven actuator disposed within the housing and operably coupled to the mass, the actuator operable to accelerate the mass along the cavity and to thereby induce a longitudinal reactive acceleration of the housing;
wherein the actuator comprises a rotary motor coupled to a transmission that converts rotary motor armature motion to linear mass motion, the transmission comprising a first gear secured to an armature of the motor, and a second gear operably coupled to the first gear and mounted to rotate about an axis perpendicular to the motor armature;
the device further including a connecting link rotatably connected to an offset pivot point of the second gear and attaching the second gear to the mass, the connecting link comprising a flex spring.

25. A sexual stimulation device, comprising:
an elongated dildo housing sized to be received within an orifice of a human body, the housing defining an internal cavity extending along a longitudinal axis of the housing;
a mass laterally constrained within the cavity and movable linearly along the cavity;
an electrically driven actuator disposed within the housing and operably coupled to the mass, the actuator operable to accelerate the mass along the cavity and to thereby induce a longitudinal reactive acceleration of the housing; and
a controller configured to control motion of the mass according to a preset motion profile including a first acceleration rate in a first direction along the longitudinal axis, and a second acceleration rate in a second directions along the longitudinal axis, the second acceleration rate differing from the first acceleration rate.

* * * * *